(12) United States Patent
Magagnoli

(10) Patent No.: US 10,206,783 B2
(45) Date of Patent: Feb. 19, 2019

(54) PROSTHETIC DEVICE FOR HUMAN BODY AND PRODUCTION METHOD THEREFOR

(71) Applicant: Augusto Magagnoli, Bologna (IT)

(72) Inventor: Augusto Magagnoli, Bologna (IT)

(73) Assignee: Cossington Limited, Kingston upon Thames, Surrey (GB)

( * ) Notice: Subject to any disclaimer, the term of this patent is extended or adjusted under 35 U.S.C. 154(b) by 0 days.

(21) Appl. No.: 14/964,621

(22) Filed: Dec. 10, 2015

(65) Prior Publication Data

US 2017/0165076 A1 Jun. 15, 2017

(51) Int. Cl.
*A61F 2/30* (2006.01)
*A61F 2/34* (2006.01)
*A61F 2/38* (2006.01)
*A61F 2/36* (2006.01)
*A61F 2/40* (2006.01)
*A61F 2/46* (2006.01)

(52) U.S. Cl.
CPC ...... *A61F 2/30771* (2013.01); *A61F 2/30942* (2013.01); *A61F 2/34* (2013.01); *A61F 2/3662* (2013.01); *A61F 2/389* (2013.01); *A61F 2/3859* (2013.01); *A61F 2/4059* (2013.01); *A61F 2002/3068* (2013.01); *A61F 2002/3069* (2013.01); *A61F 2002/3092* (2013.01); *A61F 2002/30677* (2013.01); *A61F 2002/30784* (2013.01); *A61F 2002/30822* (2013.01); *A61F 2002/30827* (2013.01); *A61F 2002/4631* (2013.01); *A61F 2310/00353* (2013.01)

(58) Field of Classification Search
CPC ............ A61B 2017/561; A61F 2/3662; A61F 2/4059; A61F 2002/30677; A61F 2002/3678; A61F 2002/3694; A61F 2002/3696; A61F 2002/30551; A61F 2002/30583; A61F 2/30767; A61F 2002/30827; A61F 2002/30879; A61F 2002/30884; A61F 2002/3068
See application file for complete search history.

(56) References Cited

U.S. PATENT DOCUMENTS

| | | | | |
|---|---|---|---|---|
| 5,250,352 | A | * 10/1993 | Tyszblat | A61C 13/0003 428/158 |
| 2006/0093646 | A1 | * 5/2006 | Cima | A61C 8/0012 424/425 |
| 2007/0259101 | A1 | * 11/2007 | Kleiner | A61L 27/30 427/2.24 |
| 2012/0172996 | A1 | * 7/2012 | Ries | A61F 2/36 623/23.44 |
| 2016/0367371 | A1 | * 12/2016 | de Beaubien | A61F 2/3609 |

* cited by examiner

*Primary Examiner* — Brian Dukert
(74) *Attorney, Agent, or Firm* — Themis Law

(57) ABSTRACT

A prosthetic device, adapted to be implanted in the human body and adapted to prevent and/or treat an infection that can arise and/or which has arisen at a bone site or at an articular site, wherein the prosthetic device has a prosthetic body provided with at least one surface for coupling, during use, with the bone or articular site and with at least one cavity placed along the coupling surface, wherein the at least one cavity is adapted to include, contain or house at least one pharmaceutical or medical substance.

13 Claims, 4 Drawing Sheets

PROSTHETIC DEVICE FOR HUMAN BODY AND PRODUCTION METHOD THEREFOR

FIELD OF THE INVENTION

The present invention concerns a prosthetic device adapted to be permanently implanted in a bone or articular site of a patient, for treating a bone lesion or a bone fracture and for the prevention and/or treatment of an infection that can arise or which has arisen in the bone or articular site of the human body.

In addition, the present invention concern a method of making a prosthetic device, adapted to be implanted in a bone or articular site of a patient, for treating a bone lesion or a bone fracture and for the prevention and/or treatment of an infection that can arise or which has arisen in the bone or articular site of the human body.

BACKGROUND OF THE INVENTION

Currently, it is known that, following the implant of a prosthesis inside the human body, a post-operation infection can arise: the prosthesis can in fact be reached by bacteria present in the implant site or in the surgical environment, which colonize the surface thereof, involving the unsticking of the prosthesis from the bone or articular site.

In these cases, the steps to be followed for defeating such infection provide for the removal of the infected prosthesis from the implant site, the implanting of an antibiotic spacer, or a spacer capable of releasing antibiotic and, finally, when the infection has been totally defeated, the installation of a new prosthesis.

The use of spacer devices is necessary in order to maintain substantially unaltered the shape of the bone site or articular site in which the new prosthesis will be implanted, as well as in order to defeat the infection underway due to the release of antibiotics.

This procedure is the re-prosthetization procedure known as "two stages" or "at two times", because the healing from the infection and the implant of a new prosthesis require two implant/treatment steps.

The use of a spacer during the "two stages" or "at two times" procedure involves the presence of several bone requirements, such as the need to have an articulation in which the ligaments are substantially integral, in a manner such that the spacer is stable once implanted, and in which the corresponding bone part has not been excessively resected, in a manner such that after the step of implant and removal of the spacer device, it is possible to fix the new prosthesis in a correct and stable position.

There is also a "one stage" surgical procedure that provides, in a single operation action, the removal of the infected prosthesis and its substitution at only one time with a new prosthesis. Nevertheless, such technique assumes the previous identification of the pathogen, in order to be able to employ, for the prosthetic re-implant, cement admixed with the specific antibiotic aimed to defeat the identified pathogen.

Such "one stage" procedure is quicker and, for this reason, involves less physical and mental stress in the patient, but it is indicated for the infections with low virulence, since it is seen that the onset of a new infection has been encountered in a—albeit small—percentage of cases. Such re-infection is instead less common in the case of the "two stages" surgical procedure.

There is therefore the need, for the surgeon, to have a prosthetic device, both first-implant and revision, provided with antibacterial power or comprising pharmaceutical or medical substances in general, such to prevent the onset of infections and/or to heal those present, and such to prevent an operation of re-prosthetization of "one stage" or "two stages" type.

SUMMARY OF THE INVENTION

The task of the present invention is to improve the state of the prior art.

In the scope of such technical task, one object of the present invention is to provide a prosthetic device capable of preventing and/or treating an infection which can arise or which has arisen at a bone site or at an articular site of the human body.

A further object of the present invention is to provide a prosthetic device for the release of at least one pharmaceutical or medical substance for long time periods and in specific portions in the bone or articular site of the human body with which it is associated.

A further object of the present invention is to provide a prosthetic device that can be either a first-implant device or a revision implant.

Another object of the present invention is to provide a first-implant antibiotic prosthetic device that clearly reduces the risk of post-operation infection of the bone or articular site, thus preventing the need for a re-prosthetization by means of "one stage" or "two stage" surgical procedure.

In accordance with one aspect of the present invention, a prosthetic device is provided as described hereinafter.

In accordance with another aspect of the present invention, a method is provided for making a prosthetic device also as described hereinafter.

Preferred and advantageous embodiments of the invention are further described hereinafter.

BRIEF DESCRIPTION OF THE DRAWINGS

Additional features and advantages of the present invention will be clearer from the detailed description of a preferred but not exclusive embodiment of a prosthetic device, illustrated by way of a non-limiting example in the enclosed drawing sheets, in which.

DETAILED DESCRIPTION OF EMBODIMENTS OF THE INVENTION

A prosthetic device according to the present invention is usable both as a first-implant prosthesis and as a revision prosthesis. Such prosthetic device is of a permanent type.

With the term "revision prosthesis", it is intended that such prosthetic device can be inserted following the explant of an infected prosthetic device, i.e. in a "one stage" surgical procedure, or after the removal of a spacer, in a "two stages" procedure. For example, such case can occur when the doctor deems that, notwithstanding the sanification of the work site of the spacer, the patient still remains at risk of re-infection; hence, the doctor decides to extensively use the final antibiotic prosthesis, or prosthesis provided with pharmaceutical or medical substances according to the present invention.

A prosthetic device according to the present invention is in fact a final prosthesis. In such sense, the prosthetic device can remain indefinitely in the human body, and be removed from the same only in exceptional circumstances (such as accidental breakage or other causes linked to the health of the patient).

More in detail, the prosthetic device performs the function of a standard prosthesis but, additionally, allows preventing the onset of a post-operation infection in the bone or articular site and/or the treatment of such site if the infection is already underway.

The prevention or treatment action occurs due to the release, by the prosthetic device, of at least one pharmaceutical or medical substance in the implant or infected zone.

A prosthetic device according to the present invention allows the release of such at least one pharmaceutical or medical substance, for example in infinitesimal amounts, for a prolonged time period: in this manner, the bone or articular site in which the implant occurs of the device itself, or the site to be treated, can absorb all the particles of the at least one pharmaceutical or medical substance released daily by the device, consequently obtaining improved prevention and/or treatment against infections. In such a manner, the risk of onset of such infections is in fact quite limited.

The configuration of the prosthetic device, as described hereinbelow, is such to allow the release of the at least one pharmaceutical or medical substance, possibly in infinitesimal quantities, in contact with or next to the bone or articular site of implant or to be treated, such that the process of absorption of such substances is efficient.

In addition, the configuration of a prosthetic device according to the invention is such to be substantially complementary to the shape of the bone or articular site of implant or to be treated.

Figure 1:
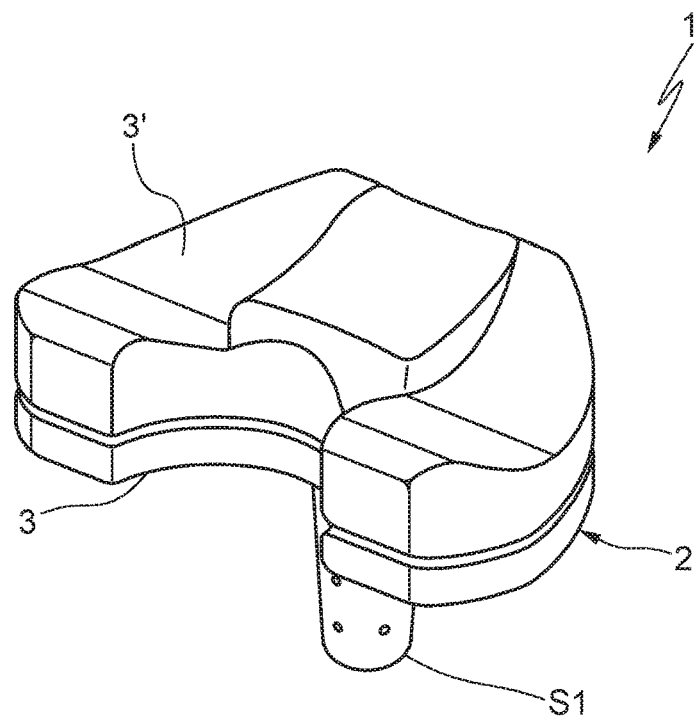
FIG. 1 is a top perspective view of one version of the prosthetic device according to the present invention.
Figure 2:
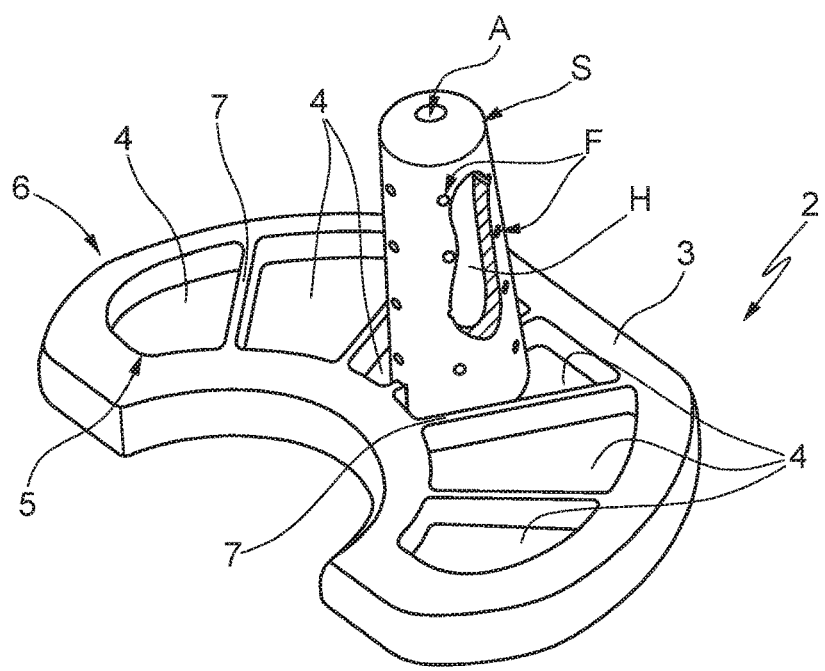
FIG. 2 is a bottom perspective view of the lower portion of the prosthetic device according to FIG. 1.
Figure 3:
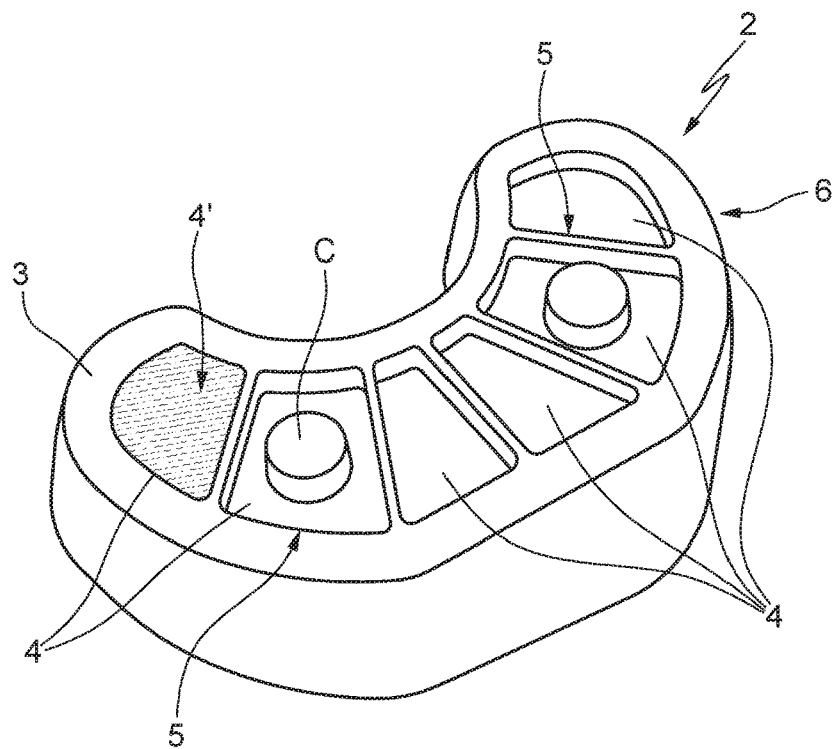
FIG. 3 is a bottom perspective view of a further embodiment of the lower portion of the prosthetic device according to FIG. 1.
Figure 4:
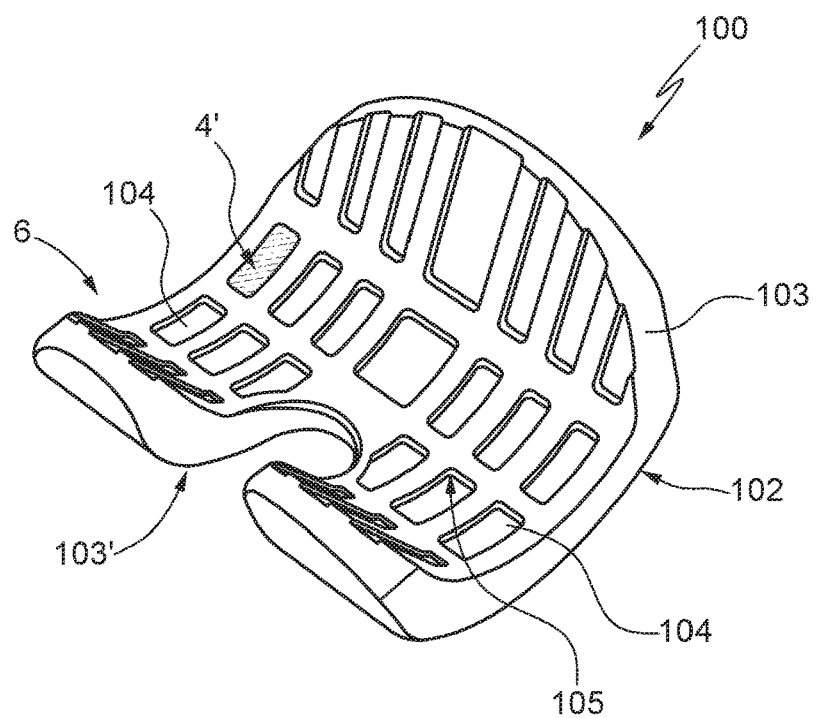
FIG. 4 is a top perspective view of a further embodiment of a prosthetic device according to the present invention.
Figure 5:
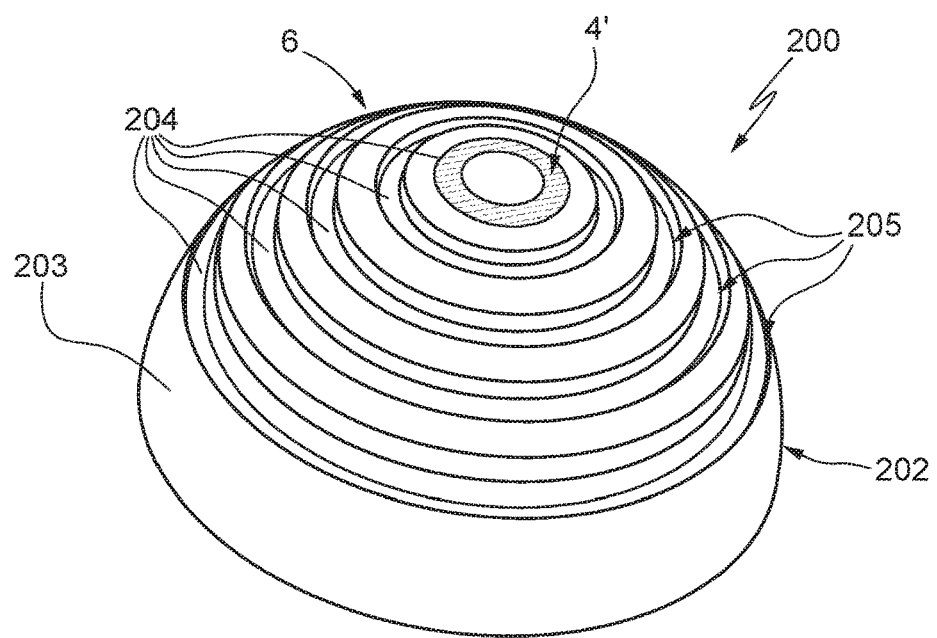
FIG. 5 is a top perspective view of an acetabular portion or version of a prosthetic device according to the present invention.
Figure 6:
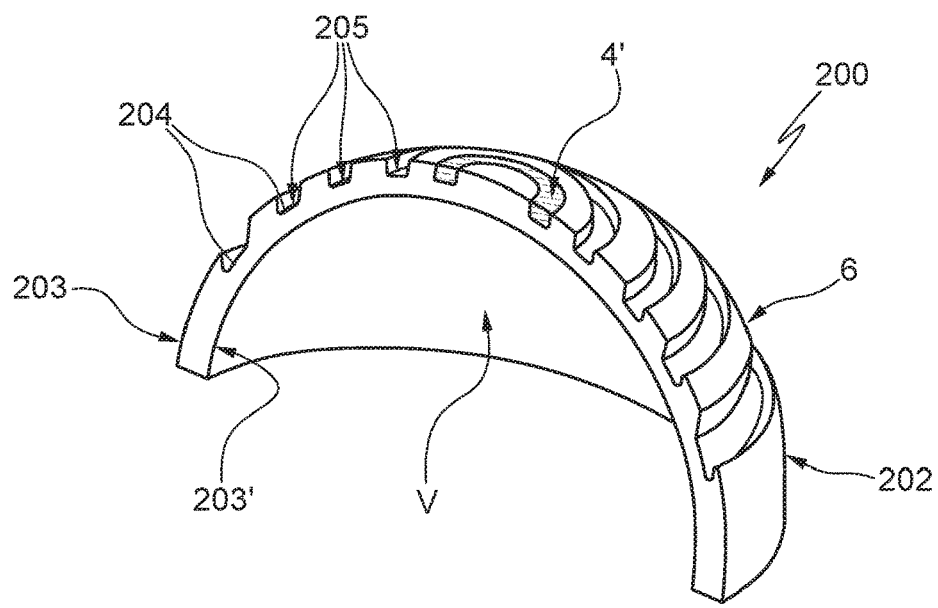
FIG. 6 is a sectional perspective view of the acetabular portion or version of a prosthetic device according to FIG. 5.
Figures 7, 8A:
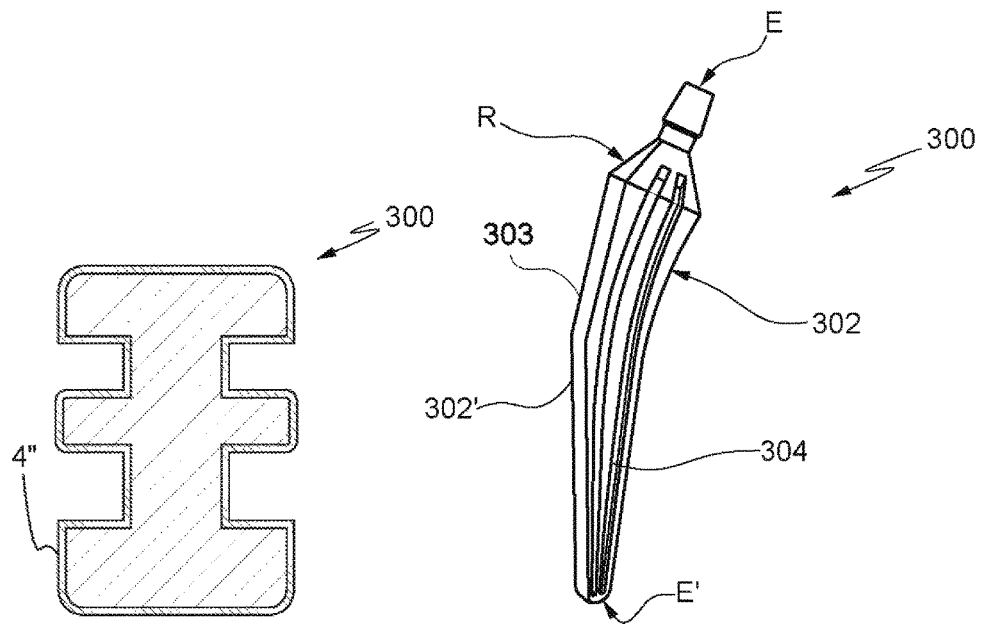
FIG. 7 is a perspective view of an additional embodiment of a prosthetic device according to the present invention.
FIG. 8A is a cross-sectional view of the prosthetic device of FIG. 8 with the filler material covering.
Figure 8:
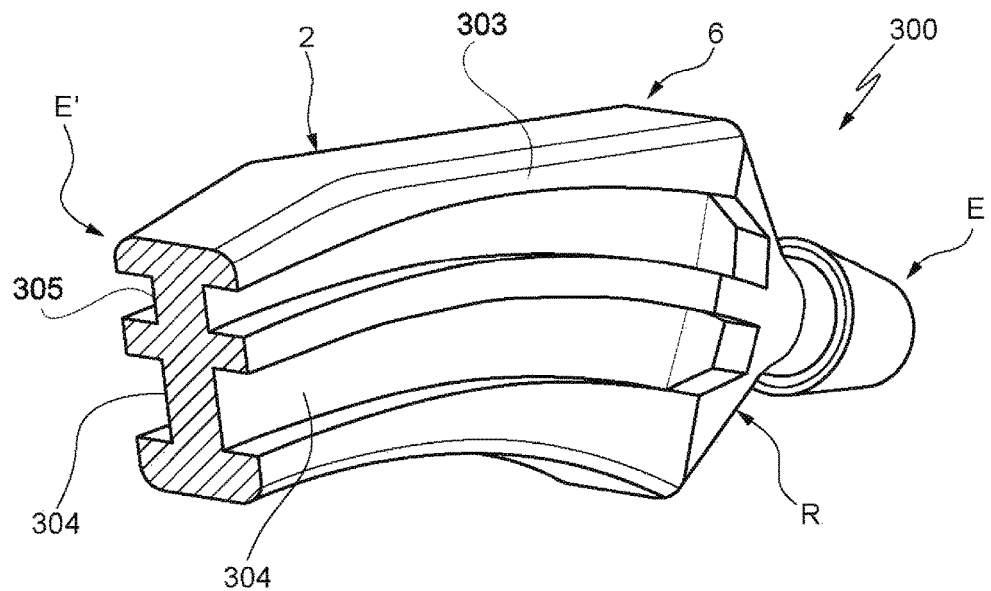
FIG. 8 is a perspective view of a prosthetic device according to FIG. 7 seen from another angle.

In the enclosed figures, several possible configurations of a prosthetic device according to the present invention are illustrated by way of a non-limiting example: in particular the prosthetic device can comprise a tibial portion of a knee prosthesis (as illustrated in FIGS. 1-3), a femoral portion of a knee prosthesis (as illustrated in FIG. 4), an acetabular portion of a hip or shoulder prosthesis (as shown in FIGS. 5 and 6), a stem-like portion of a hip or shoulder prosthesis (as illustrated in FIGS. 7 and 8) or a bone prosthesis in general.

A prosthetic device according to the present invention is made of a material that is biologically-compatible with human tissues. For example, such material can be a metal, a metal alloy, an organo-metallic compound, a ceramic or a combination thereof.

In one version of the present invention, the biologically-compatible material can comprise or be at least partially covered with acrylic resin, plastic material, ceramic material, resin with high porosity, bone cement or polymethylmethacrylate (PMMA), thermoplastic polymers, polyethylene, polypropylene, polyester, thermoforming polymers, or a combination thereof or other similar materials The covering can cover, in one version of the invention, only some portions of the prosthetic device, generally those most subjected to rubbing.

In addition, the portions most subjected to wear can have a covering that confers greater hardness thereto, which can be obtained by means of deposition or application of at least one metal oxide and/or nitride, e.g. titanium nitride.

In an alternative version of the invention, instead, the covering can cover the entire surface of the prosthetic device adapted to be positioned, during use, in contact with the bone tissue of the patient.

For the obtainment of the prosthetic device according to the present invention, nevertheless, further materials of biocompatible type are usable, with respect to that described above, without departing from the protective scope of the present invention.

With reference to the enclosed FIGS. 1-3, a prosthetic device according to the present invention comprising a tibial component of a prosthesis for the knee joint is indicated overall with reference number 1.

The prosthetic device 1 comprises at least one prosthetic body 2.

Such prosthetic body 2 has a shape substantially complementary to that of the bone or articular site in which it must be implanted, or which in any case is to be treated.

In particular, the prosthetic body 2 comprises a tibial plate and, possibly, a stem-like component S.

The stem S has a substantially tubular shape while the tibial plate component 20 has a substantially flat "C" shape.

In such a manner, the positioning of the prosthetic device 1 in the bone or articular site is precise and the obtained performances are optimal.

The prosthetic device 1 is adapted to be constrained to the tibial end of the knee joint.

Specifically, the stem S is adapted to be inserted within the tibial medullary canal, at the knee joint.

Such stem S is hollow and internally has a cavity H; the stem S also comprises holes F, passing through the wall of the stem S itself, adapted to supply at least one pharmaceutical or medical substance, contained in the cavity H of the stem S or in a filler material 4' contained in the cavity H, towards the implant site of the prosthetic device 1 or towards the site to be treated.

Such pharmaceutical or medical substance can be inserted within such stem S by means of an opening A, of greater size than the holes F, placed at the stem itself. Such opening A is in particular placed in the distal end 51 of the stem S, adapted during use to be inserted in the tibial medullary canal at the knee joint. The prosthetic body 2 is provided with at least one coupling surface 3 adapted to come into contact with the bone or articular site to be treated.

The opening A is placed in a continuous manner with the cavity H of the stem S.

The configuration of such coupling surface 3 is substantially complementary to the bone or articular site of the patient, such that the positioning and connection of the prosthetic device 1 in/to the bone or articular site is correct.

In addition, in one version, the coupling surface 3 is, during use, completely in contact with the bone tissue.

The coupling surface 3, as shown in FIGS. 1-3, is shaped in a manner such to allow the coupling of the prosthetic body 2 to the tibial end at the knee joint.

The prosthetic body 2, in particular the coupling surface 3, has at least one cavity 4.

According to one version of the invention, such cavity 4 is a groove.

Such at least one cavity 4, according to one version of the invention, is adapted to comprise, contain or house a filler material 4'.

According to a further version of the present invention, the coupling surface 3 can be totally covered with filler material 4'. In such case, the coupling surface 3 comprises a filler material covering 4' placed at and in contact with the entire coupling surface 3 itself.

In one version of the invention, the stem S comprises a filler material covering 4' placed at and in contact with the entire of the stem S itself, adapted to be placed during use in contact with the bone tissue of the patient. When it covers the stem S, the filler material covering 4' must have, in one version of the invention, a hard and/or compact consistency. For example, it is possible to use, in order to obtain such filler material covering 4', porous ceramic, terracotta, plastic materials or materials with hard consistency. Such materials are capable of ensuring a certain strength. At any rate, the covering is porous or comprises small channels, in a manner such that the prosthetic device 1, once immersed in a medicated solution or a solution containing a pharmaceutical or medical substance, is capable of being impregnated therewith.

Such filler material 4' can be in solidifiable fluid form or in solid form.

In one version of such invention, the filler material 4', placed in the at least one cavity 4, is hardened.

In addition, the filler material 4' occupies the entire space corresponding with the at least one cavity 4 and hence completely fills it.

Alternatively, the filler material 4' occupies the entire coupling surface 3 adapted to be placed during use in contact with the bone tissue of the patient.

The use of filler material 4' at least partially ensures the restoration of the mechanical as well as geometric properties of a prosthetic device of conventional type.

In one version of the invention, the filler material 4' comprises or can be admixed with at least one pharmaceutical or medical substance.

More in detail, such filler material 4' can be, at the start, without pharmaceutical or medical substances, in a manner such that at least one pharmaceutical or medical substance can be admixed with the filler material itself during the surgical step (also based on the needs of the patient and the state of the encountered infection).

Alternatively, the filler material 4' can comprise at least one pharmaceutical or medical substance, in a manner such that such material 4' can be inserted within the cavity/cavities 4 without having to add any substance necessary for treating the infection (possibly, for specific needs, such filler material 4' can be admixed with further substances, in addition to those already comprised therein).

Therefore, such filler material 4' can comprise at least one pharmaceutical or medical substance or it can be admixed with such substances.

In one version of the invention, such filler material 4' can comprise at least one from among the following materials: acrylic resin, composite material comprising calcium phosphate or an inorganic salt, calcium sulphate, bioglass, polyvinyl alcohol, or a mixture thereof.

In another version of the invention, the filler material 4' can comprise absorbent material, for example silk thread, cotton thread or biocompatible plant fiber, or a non-woven fabric capable of absorbing and being impregnated with at least one pharmaceutical or medical substance, e.g. antibiotic.

In a further version, such filler material 4' comprises a biocompatible semi-solid material which comprises a pharmaceutical or medical substance, such as an antibiotic.

In the aforesaid case, the semi-solid material can be insoluble (e.g. bone cement) or soluble (e.g. animal collagen, sugars, cellulose, etcetera).

In addition, such filler material 4' can be porous or comprise pores or small channels. Such pores must have size suitable for preventing bone growth within the material itself According to a still further version, the filler material 4' can coincide with the material constituting the prosthetic body 2.

The filler material 4' has, substantially for its entire volume, a plurality of small channels with dimensions on the order of one micrometer (if the dimension is considered that is perpendicular to that of greater extension of the small channel itself).

Such small channels can absorb and elute liquids via capillarity.

In one possible configuration, the small channels are interconnected with each other.

In addition, in one version, such small channels and/or such pores can have average size in cross section of about 100 micron.

In a preferred version of the present invention, the filler material 4' comprises an acrylic resin and an inorganic salt, e.g. PMMA (polymethylmethacrylate) and calcium phosphate or tri-calcium phosphate (TCP).

In one possible configuration, as shown in FIGS. 1-3, the prosthetic device has a plurality of cavities 4 placed along the coupling surface 3.

According to a non-illustrated version, the depth of the cavities 4 within the prosthetic body 2 can be variable with respect to each other within a same device 1.

In addition, the positioning of the cavities 4, their number and their shape can vary as a function of specific requirements.

The size of the cavities 4 can in any case also be variable as a function of the size of the prosthetic body 2.

Each cavity 4 constitutes a corresponding opening 5 that is extended through the coupling surface 3.

In one embodiment, as shown in FIG. 3, some cavities 4 can have C elements adapted to allow the identification of the correct positioning of the prosthetic device 1 in the bone or articular site. In such case, it is possible for example that there is an interaction with a collimation mask or template of an instrument specific for the prosthesis in question.

As already mentioned above, the at least one cavity 4 acts as a housing for a filler material 4'. Indeed, within at least one opening 5 or only in some openings 5, if there are a plurality of cavities 4 in the prosthetic body 2, a filler material 4' is comprised, contained or housed, which can comprise at least one pharmaceutical or medical substance which is released inside the human body of the patient.

In one possible version of the invention, the filler material 4' is prepared and positioned in the cavity/cavities 4 by the surgeon before the implant of the prosthetic device itself, i.e. during the operation procedure.

The prosthetic device 1, as stated, has configuration such to ensure that the filler material 4' is in contact with the bone or articular tissues to be treated or of implant; consequently, such filler material 4' fills such cavity 4 such to be flush with the coupling surface 3 or projecting with respect to such coupling surface 3. In such a manner, a surface continuous with the coupling surface 3 of the prosthetic body 2 is obtained.

In accordance with the time period estimated to be necessary for the release of at least one pharmaceutical or medical substance in the bone or articular site of implant, the overall volume occupied by the at least one cavity 4 can vary, such that the prosthetic device 1 can ensure the release of at least one pharmaceutical or medical substance for the entire selected period.

In a further version of the present invention, the prosthetic device 1, at the coupling surface 3, comprises a cavity 4 of size substantially corresponding with that of the coupling surface 3 itself: such cavity 4 is filled with the filler material 4'.

The configuration of the cavities 4 can be such to define an open-cell structure 6 along the coupling surface 3.

The open-cell structure 6 comprises a plurality of cells placed next to each other, each of which corresponding with the cavities 4.

The open cells 6 or the cavities 4 are separated from each other by ribs 7.

Such ribs 7 represent walls interposed between the cavities 4 themselves or between the cells 6 themselves, which allow a physical division of the spaces defined by such cavities 4 or cells 6.

In one version of the invention, the ribs 7 or at least one rib 7 determines the perimeter of the cavities 4 or of the open cells 6.

The ribs 7 project upward in a substantially perpendicular manner from an internal wall of the open cells 6 or of the cavities 4.

The ribs 7 can also act as reinforcement elements for the prosthetic body 2. Based on this further function of the ribs 7, the cavities 4 can have a positioning such to ensure the presence of the ribs 7 at the portions of the prosthetic device 1 which, during use, are subjected to greater mechanical stresses, e.g. wear, bending, fatigue, etc.

In addition, it is possible that such cavities 4 or cells 6 contain filler material 4' that is different from one cavity to another, or a material 4' containing at least one pharmaceutical or medical substance that is different from one cavity to another. In this manner, it is possible to carry out a preventative or curative treatment that is differentiated for the different areas of the bone or articular site.

According to a further version not shown in the enclosed figures, some or all the cavities 4 or cells 6 can be in communication with each other, e.g. by means of perforations placed at the ribs 7.

In accordance with the shape of the coupling surface 3, i.e. in accordance with the type of prosthetic device 1 considered, the distance along with the mutual positioning between the single cavities 4 can vary.

As shown in FIG. 1, the prosthetic body 2 can be associated with an insert 3'.

Such insert 3' can be made of plastic or polymer material, such as polyethylene, polypropylene, polyester, and other similar materials.

In particular, the insert 3' is made of a material capable of facilitating the sliding or articulation with a further prosthetic component or with the bone tissue of the patient, at the specific joint or implant site.

For example, in order to make the tibial insert 3', polyethylene UHMWPE can be used, which is a low-friction material.

Such insert 3', in one version of the invention, is positioned on the prosthetic body 2 in an opposite position with respect to the coupling surface 3, which comes into contact with the bone or articular site.

The insert 3' and the prosthetic body 2 can have a variable positioning with respect to each other, in accordance with the shape of the prosthetic device itself.

According to a configuration not shown in the figures, the insert 3' may possibly have at least one further cavity.

In FIG. 4, an additional embodiment is illustrated of a prosthetic device that during use can be constrained to the femoral end of the knee joint; such device is indicated overall with the reference number 100.

Hereinbelow, the same components corresponding with those of the previously-described embodiment will be indicated with the same reference numbers increased by one hundred.

The prosthetic device 100 overall differs from the preceding prosthetic device, indicated with number 1, only due to its configuration, since such device 100 represents a prosthesis associable with the lower end of the femur, at the knee joint.

The prosthetic device 100 is adapted, in one version of the invention, to be articulated during use with the prosthetic device 1, or better yet with its possible insert 3'.

The prosthetic device 100 comprises a prosthetic body 102 in turn comprising at least one surface 103 for coupling, during use, with the femoral bone end at the knee joint.

The prosthetic body 102 has a substantially "U" shape.

In particular, the coupling surface 103 corresponds with the concave surface of the prosthetic body 102.

In addition, the prosthetic body 102, or better yet its coupling surface 103, comprises at least one cavity 104.

The at least one cavity 104 determines a respective opening 105, which is extended along and/or through the at least one coupling surface 103.

According to one aspect of the present invention, each cavity 104, hence each opening 105, can comprise, contain or house a filler material 4'.

The shape, volume and arrangement of the single cavities 104 can vary, for example based on the shape of the prosthetic body 102.

In a preferred embodiment, the configuration of such cavities 104 or openings 105 is an open-cell 6 configuration.

The prosthetic device 100 comprises an articulation surface 103" opposite the coupling surface 103.

The articulation surface 103" corresponds with the convex surface of the prosthetic body 102.

Such articulation surface 103" is adapted to be associated, in an articulated manner, with the tibial portion of the knee joint or with the articulation surface or with the insert 3' of the prosthetic device 1.

The articulation surface 103" may possibly house further cavities, not shown in FIG. 4.

The characteristics of the cavities 104, of the material 4' and of the openings 105 correspond with those previously described for the prosthetic device 1.

In FIGS. 5 and 6, a further version of the present invention is shown in which the prosthetic device, indicated overall with reference number 200, comprises a cotyloid or an acetabular portion of a hip or shoulder prosthesis. The prosthetic device 200 comprises a prosthetic body 202.

Such embodiment has the same characteristics described for the previous embodiments, but varies regarding configuration since the implant site is different than that of the prosthetic devices 1 and 100.

Hereinbelow, the same components corresponding with those of the previously-described embodiments will be indicated with the same reference numbers increased by one hundred.

The prosthetic body 202 has a dome-like or hemisphere-like configuration.

The prosthetic body 202 subtends an empty space or concavity V.

The empty space or concavity V has a hemispherical shape and is adapted to house during use a head of a hip or shoulder prosthesis or the bone portion of the head of the femur or of the shoulder bone, given that they are substantially complementary thereto.

The prosthetic body 202, during use, is adapted to be positioned and/or fixed in/to the acetabular or cotyloid cavity which is present at the human pelvis or the shoulder joint.

The prosthetic body 202 comprises a coupling surface 203 and an internal or articulation surface 203' opposite the coupling surface 203.

The coupling surface 203 is convex, corresponds with the convex surface of the prosthetic body 202 and is adapted to come into contact with the bone of the patient.

The internal surface 203' is concave, corresponds with the concave surface of the prosthetic body 202 and is instead adapted to make the articulation of the corresponding bone site. The concavity of the articulation surface 203' corresponds with the empty space or concavity V.

An articular insert, not illustrated in the figures, made of material of various types, e.g. ceramic or polyethylene, can be positioned in contact with the internal surface 203', in a manner such to decrease the friction caused by the articulation.

The coupling surface 203 comprises one or at least one cavity 204. The at least one cavity 204 can have variable volume, configuration and/or arrangement in accordance with the geometry of the prosthetic body 202 and in accordance with the requirements.

In one version of the invention, the at least one cavity 204 can assume the configuration of at least one annular groove.

Such grooves can be arranged at a constant distance from each other. Such grooves can be positioned in a concentric manner and parallel to a diameter of the prosthetic body 202.

In a further embodiment, the at least one cavity 204 is arranged in a non-uniform manner along the coupling surface 203, and the cavities have shapes and volumes different from each other.

Each cavity 204 determines a corresponding opening 205 which is extended through the coupling surface 203.

The openings 205 correspond with a space within which it is possible to house the filler material 4'.

Also in this case, in one version of the invention the coupling surface 203 can comprise a filler material covering 4', of size analogous to that of the coupling surface itself In FIGS. 7 and 8 a further version of the present invention is represented, in which a prosthetic device 300 comprises a prosthetic body 302 which has a stem-like shape.

The prosthetic body 302 has an elongated shape and is adapted to constitute the stem of a hip or shoulder prosthesis.

The prosthetic device 300 can comprise, in the version relative to a hip prosthesis, a head corresponding to the femoral head of the hip joint, adapted to be articulated with the cotyloid of a patient or with the prosthetic device 200.

The prosthetic body or stem 302 comprises an end E. The end E represents the proximal end of the prosthetic body 300, adapted to be coupled with the head of the prosthesis, when present.

In addition, the prosthetic body 300 comprises a distal end E', opposite during use with respect to the end E. The distal end E' is adapted to be implanted within the femoral medullary canal or in the shoulder bone of the patient.

In the embodiment shown in FIGS. 7 and 8, the proximal end E has a frustoconical shape. Such shape is however non-limiting of the present invention and the end E can also have other shapes or forms.

The prosthetic body 300 further comprises a connector portion R, placed at the proximal end E and adapted to connect the proximal end E with an elongated body 302' which constitutes the stem-like element of the prosthetic body 302.

The prosthetic body 302 or the stem-like element 302' comprises at least one coupling surface 303, adapted to come into contact during use with the bone stem or the implant bone site.

Along such coupling surface 303, one or at least one cavity 304 is present that is adapted to comprise, contain or house the filler material 4'.

In one version of the invention, the at least one cavity 304 has a groove-like shape. In particular, such at least one groove has a longitudinal progression, parallel to the longitudinal axis of the stem-like element 302' of the prosthetic body 302.

Each groove or cavity 304 identifies a respective opening 305.

Also in this case, the at least one cavity 304 has geometry, volume and/or arrangement that varies in accordance with the implant site or in accordance with requirements.

In the version shown in FIGS. 7 and 8, the cavities 304 appear as grooves having an extension equal to the distance from the portion R up to the distal end E' of the stem-like element or prosthetic body 302.

In an alternative version, not illustrated in the figures, such cavities 304 could have a partial or zonal extension.

In addition, in the version illustrated in FIGS. 7 and 8, in which the prosthetic body 2 has a stem-like element with substantially rectangular cross section, having two opposite faces with greater width than the other opposite faces, the at least one cavity 304 can be placed at the faces of greater size. Such configuration, nevertheless, is only a non-limiting example of the present invention.

In a still further version, shown in FIG. 8A, the stem 302' comprises a filler material covering 4" placed at and in contact with the entire surface of the stem itself, adapted to be placed during use in contact with the bone tissue of the patient. When it covers the stem 302', the filler material covering 4" must have, in one version of the invention, a hard and/or compact consistency. For example, it is possible to use, in order to obtain such filler material covering 4", porous ceramic, terracotta, plastic materials or materials with hard consistency, i.e. materials capable of ensuring a certain strength. At any rate, the covering is porous or comprises small channels, in a manner such that the prosthetic device 1, once immersed in a medicated solution or a solution containing a pharmaceutical or medical substance, is capable of being impregnated therewith.

The invention thus conceived allows obtaining technical advantages.

First of all, the advantage of being able to use a prosthesis which, with respect to the conventional prostheses, allows a prevention and/or a treatment of the bone or articular infections, without having to intervene with a one-stage or two-stage treatment.

In addition, notwithstanding the presence of the at least one cavity filled with filler material, a prosthetic device is obtained with mechanical characteristics comparable to those of the standard prostheses.

In addition, the presence of cavities which can be independent from each other allows arranging a prosthetic device capable of releasing more than one type of pharmaceutical or medical substance in the bone or articular site to be treated. The present invention then regards a method for making a prosthetic device 1, 100, 200, 300.

Such method provides for the steps of obtaining a prosthetic body 2, 102, 202, 302 having a shape substantially complementary to that of the bone or articular site of implant or to be treated and provided with at least one cavity 4, 104, 204, 304, of providing at least one filler material 4' comprising at least one pharmaceutical or medical substance or admixable with at least one pharmaceutical or medical substance, of inserting, in the at least one cavity 4, 104, 204, 304, the at least one filler material 4'.

In one version of the invention, the method comprises the steps of obtaining a prosthetic body 2, 102, 202, 302 having a shape substantially complementary to that of the bone or articular site of implant or to be treated, of providing at least one filler material 4' comprising at least one pharmaceutical or medical substance or admixable with at least one pharmaceutical or medical substance, of covering at least one coupling surface 3, 103, 203, 203 of the prosthetic body 2, 102, 202, 302 with the at least one filler material 4'.

The filler material 4' comprises or can be admixed with or is capable of absorbing or being impregnated with at least one pharmaceutical or medical substance. Therefore, the method can provide for immersing or impregnating the filler material 4' with the at least one pharmaceutical or medical substance. In this manner, the accumulation of the pharmaceutical or medical substance is determined in the porous material contained in the prosthesis according to the present invention. The accumulated pharmaceutical or medical substance, once the prosthesis will be implanted in the bone, will exit or elute from the prosthetic material and will enter into the periprosthetic tissues, medicating them.

The method can further comprise a step of waiting for the filler material 4'—which can be of solidifiable type (e.g. bone cement)—to harden, making a single body with the prosthetic body 2, 102, 202, 302 itself, or a step of solidifying the filler material 4', in a manner such that the filler material 4' forms a single body with the prosthetic body 2, 102, 202, 302.

The method can also provide for a step of providing at least one insert 3' and associating or fixing the insert 3' with the prosthetic body 2, 102, 202, 302, and/or positioning a possible insert 3' and coupling the insert 3' with the prosthetic body 2, 102, 202, 302, thus determining an articulation surface with another prosthetic component or with the bone tissue having limited friction.

In one version of the invention, the method can comprise the steps of arranging at least one pharmaceutical or medical substance and immersing or impregnating the prosthetic device within the at least one pharmaceutical or medical substance.

Finally, the prosthetic device 1, 100, 200, 300 is during use implanted at the bone or articular site.

Once in place, the prosthetic device 1, 100, 200, 300 gradually releases, in a substantially uniform manner, the at least one pharmaceutical or medical substance present therein, at the implant site or at the site to be treated.

The prosthetic device 1, 100, 200, 300 is permanent.

Also the aforesaid method allows obtaining technical advantages.

Firstly, such method allows obtaining, in a few simple steps, a prosthetic device capable both of preventing and treating an infection of the bone or articular site.

Secondly, the described method allows arranging a prosthetic device effective in preventing and treating infections of the bone or articular site: such device in fact contains at least one pharmaceutical or medical substance, to be released at the bone or articular site, in a manner so as to prevent the onset of an infection or to defeat it, when it is already underway.

The invention thus conceived is susceptible of numerous modifications and variants, all falling within the scope of the inventive concept.

The characteristics present for one version or embodiment can be combined with the characteristics of another version or embodiment, without departing from the protective scope of the present invention.

As is seen, the prosthetic device according to the present invention comprises, contains, houses or is admixable with at least one pharmaceutical or medical substance, for example at least one antibiotic. In such a manner, such pharmaceutical or medical substance—accumulated at the interface or within the prosthetic device itself, once the device during use is implanted in the human body—will exit from or be eluted from the material of the prosthetic device itself. The treatment or the medication of the bone tissues surrounding the prosthetic device is thus obtained, as the at least one pharmaceutical or medical substance comes into contact with such bone tissues.

In one version of the invention, a kit is provided comprising a prosthetic device according to the present invention and a filler material of the above-described type.

In one version of the invention, the prosthetic device according to the present invention is preformed. According to such aspect, with the definition of preformed it is intended a prosthetic device already provided with the filler material 4' on the at least one coupling surface. The preformed prosthetic device is therefore already provided with filler material when sold, and hence it is ready for use.

In addition, all the details can be substituted with technically equivalent elements.

In practice, the materials used as well as the contingent shapes and size can be of any type, according to the requirements, without departing from the protective scope of the following claims.

The invention claimed is:

1. A prosthetic device, implantable in a bone or articular site of a human body, comprising:
    a prosthetic body, said prosthetic body comprising at least one coupling surface adapted to come into contact during use with said bone or articular site,
    wherein said at least one coupling surface comprises at least one cavity containing a filler material comprising at least one pharmaceutical or medical substance, said filler material being solid or in a solidifiable fluid form and having the at least one pharmaceutical or medical substance contained therein that prevents or treats infections, said filler material further having pores or channels dimensioned to prevent bone growth within the filler material, wherein said filler material occupies an entire space defined by said at least one cavity, thereby completely filling said at least one cavity, and wherein said filler material is flush with, or projecting from, said at least one coupling surface.

2. The prosthetic device according to claim 1, wherein said at least one coupling surface of said prosthetic body comprises a plurality of cavities adjacent to each other, in a manner so as to define an open-cell structure along said coupling surface.

3. The prosthetic device according to claim 2, wherein said open cells or cavities are separated from each other by ribs and/or have a perimeter formed by at least one rib.

4. The prosthetic device according to claim 3, wherein said ribs comprise walls interposed between said open cells or cavities, projecting upward in a substantially perpendicular manner from an internal wall of said open cells or cavities.

5. The prosthetic device according to claim 1, wherein said prosthetic body is made of a biologically-compatible material.

6. The prosthetic device according to claim 5, wherein said biologically-compatible material comprises or is at least partially covered with acrylic resin, plastic material, ceramic material, resin with high porosity, bone cement or polymethylmethacrylate (PMMA), thermoplastic polymers, polyethylene, polypropylene, polyester, thermoforming polymers, metal oxides and/or nitrides, such as titanium nitride or a combination thereof or porous ceramic, plastic materials, or a material having a hard consistency.

7. The prosthetic device according to claim 1, wherein said filler material comprises an acrylic resin, a composite material comprising calcium phosphate or an inorganic salt, calcium sulphate, bioglass, polyvinyl alcohol, a mixture thereof, or an absorbent material.

8. A prosthetic device, implantable in a bone or articular site of a human body, comprising:

a prosthetic body, said prosthetic body comprising at least one coupling surface adapted to come into contact during use with said bone or articular site, wherein said at least one coupling surface comprises at least one cavity containing a filler material comprising at least one pharmaceutical or medical substance that prevents or treats infections, said filler material being solid or in a solidifiable fluid form and having the at least one pharmaceutical or medical substance contained therein, said filler material further having pores or channels dimensioned to prevent bone growth within the filler material, and wherein said at least one coupling surface comprises at least one covering of the filler material placed at, or in contact with, an entirety of the at least one coupling surface, thereby being in contact with tissue of the bone or articular site.

9. The prosthetic device according to claim 1, wherein said pores or channels gave an average size in cross section of about 100 micron.

10. The prosthetic device according to claim 1, wherein said filler material is made of a same material as the prosthetic body.

11. The prosthetic device according to claim 8, wherein said pores or channels gave an average size in cross section of about 100 micron.

12. The prosthetic device according to claim 8, wherein said filler material is made of a same material as the prosthetic body.

13. A prosthetic device, implantable in a bone or articular site of a human body, comprising:

a prosthetic body, said prosthetic body comprising at least one coupling surface adapted to come into contact during use with said bone or articular site, and a filler material comprising at least one pharmaceutical or medical substance that prevents or treats infections, said filler material being solid or in a solidifiable fluid form and having the at least one pharmaceutical or medical substance contained therein, said filler material further having pores or channels dimensioned to prevent bone growth within the filler material, wherein said at least one coupling surface comprises at least one covering of the filler material comprising the at least one pharmaceutical or medical substance, and wherein said filler material is flush with said at least one coupling surface.

\* \* \* \* \*